United States Patent [19]

Werne

[11] Patent Number: 5,782,764

[45] Date of Patent: Jul. 21, 1998

[54] FIBER COMPOSITE INVASIVE MEDICAL INSTRUMENTS AND METHODS FOR USE IN INTERVENTIONAL IMAGING PROCEDURES

[75] Inventor: Roger W. Werne, San Ramon, Calif.

[73] Assignee: ITI Medical Technologies, Inc., Livermore, Calif.

[21] Appl. No.: 754,506

[22] Filed: Nov. 19, 1996

Related U.S. Application Data

[63] Continuation-in-part of Ser. No. 554,446, Nov. 7, 1995.

[51] Int. Cl.$^6$ .............. A61B 5/05; A61B 10/00
[52] U.S. Cl. ............ 600/411; 600/420; 600/427; 600/431; 600/458; 600/562; 600/567
[58] Field of Search .................. 128/653.1, 653.2, 128/653.4, 653.5, 654, 749, 754; 600/411, 420, 423, 427, 431, 562, 567, 458

[56] References Cited

U.S. PATENT DOCUMENTS

| | | | |
|---|---|---|---|
| 4,572,198 | 2/1986 | Codrington | 128/653 |
| 4,827,931 | 5/1989 | Longmore | 128/334 R |
| 4,917,100 | 4/1990 | Nottke | 128/754 |
| 4,984,573 | 1/1991 | Leunbach | 128/653 |
| 4,989,608 | 2/1991 | Ratner | 128/653 A |
| 5,081,997 | 1/1992 | Bosley, Jr. et al. | 128/662.02 |
| 5,154,179 | 10/1992 | Ratner | 128/653.4 |
| 5,155,435 | 10/1992 | Kaufman et al. | 324/309 |
| 5,209,750 | 5/1993 | Stef | 606/54 |
| 5,211,166 | 5/1993 | Sepponen | 128/653.5 |
| 5,218,964 | 6/1993 | Sepponen | 128/653.2 |
| 5,262,727 | 11/1993 | Behbin et al. | 324/318 |
| 5,269,305 | 12/1993 | Corol | 128/653.1 |

(List continued on next page.)

FOREIGN PATENT DOCUMENTS

| | | |
|---|---|---|
| 0 174 011 A2 | 3/1986 | European Pat. Off. |
| 0 566 359 A2 | 10/1993 | European Pat. Off. |
| WO 96/14023 | 5/1996 | WIPO |
| WO 97/07746 | 3/1997 | WIPO |

OTHER PUBLICATIONS

Jolesz, et al., "Interventional Use of Magnetic Resonance Imaging," Magnetic Resonance Quarterly, vol. 10, No. 2, pp. 85–96 (1994).

Bunshah, et al., *Deposition Technologies for Films and Coatings*, Noyes Publications, Park Ridge, New Jersey, pp. 85 and 170–172 (1982).

Brookes, et al., "Artifact–Free MR Imaging–Compatible Needle." 82nd Scientific Assembly and Annual Meeting of the Radiological Society of North America, Chicago, Illinois, p. 210 (Nov. 11, 1996).

*Primary Examiner*—Ruth S. Smith
*Attorney, Agent, or Firm*—Limbach & Limbach L.L.P.

[57] ABSTRACT

A medical interventional instrument for use in a magnetic resonance imaging (MRI) or other imaging system, a method for designing such an instrument, and a method including the steps of positioning an instrument having a body with a contrast region (constructed in accordance with the invention) and a target in the imaging region of an imaging system and operating the imaging system to produce an image showing both the target and the contrast agent. The instrument has a carbon-fiber or glass-fiber composite (or zirconia) body which preferably carries a contrast agent which is appropriate to the particular imaging modality to be used with the instrument. The concentration and volume of the contrast agent are determined (preferably experimentally) to cause the instrument to be positively shown in an image produced by the imaging system, without obscuring or distorting unacceptably the image of the target (e.g., a typical target, such as human tissue) with which the contrast agent is to be imaged. In some preferred embodiments, the contrast agent is a paramagnetic metal ion. In other preferred embodiments, the contrast agent is an iodinated hydrocarbon. In further preferred embodiments, the contrast agent is a preparation containing microbubbles of air or other gas, or the contrast region includes an air-filled void.

22 Claims, 6 Drawing Sheets

U.S. PATENT DOCUMENTS

| | | | |
|---|---|---|---|
| 5,271,400 | 12/1993 | Dumoulin et al. | 128/653.2 |
| 5,290,266 | 3/1994 | Rohling et al. | 604/272 |
| 5,318,025 | 6/1994 | Dumoulin et al. | 128/653.2 |
| 5,353,795 | 10/1994 | Souza et al. | 128/653.2 |
| 5,357,958 | 10/1994 | Kaufman | 128/653.2 |
| 5,409,003 | 4/1995 | Young | 128/653.2 |
| 5,534,778 | 7/1996 | Loos et al. | 324/318 |

FIBER COMPOSITE INVASIVE MEDICAL INSTRUMENTS AND METHODS FOR USE IN INTERVENTIONAL IMAGING PROCEDURES

CROSS-REFERENCE TO RELATED APPLICATION

The present application is a continuation-in-part of pending U.S. patent application Ser. No. 08/554,446, filed Nov. 7, 1995.

FIELD OF THE INVENTION

The invention pertains to the use of medical invasive devices made of carbon-fiber (or glass-fiber) composites in applications, such as interventional imaging procedures, in which a target (e.g., a human patient or animal) and an interventional instrument (e.g., a biopsy needle or catheter) are present within the field of view of the imaging system. In preferred embodiments, the invention is an interventional instrument made of carbon-fiber whose structure incorporates a contrast agent which allows a segment of the device to be visualized by a medical imaging system without distorting or obscuring the image of the target also being imaged by the medical imaging system. The invention also pertains to a method for using such an instrument.

BACKGROUND OF THE INVENTION

Medical therapy performed on a patient while the patient is being imaged using a diagnostic imaging modality is generally referred to as interventional radiology or interventional imaging. In interventional radiological procedures, the patient and at least one instrument necessary to perform a therapeutic or diagnostic function, are positioned in the imaging region of an imaging system. Examples of instruments used in interventional radiology are scalpels, forceps, retractors, biopsy needles, catheters, and the like. Implanted devices used for therapy such as sutures, pacemakers, stents, shunts, orthopaedic devices, dental devices and the like are also examples of such instruments. It is necessary that the presence of these devices does not lead to a degradation or distortion in the images obtained which would lead to a loss in diagnostic yield. Further, it is often desired that the interventional imaging system portray one or more of the instruments while also imaging a selected portion of the patient. For example, it may be desirable to visualize a biopsy needle or catheter inserted into the tissue of the patient. In addition, it is also desirable to have permanently implanted medical devices such as blood filters, stents, or other such implants which do not distort or degrade the images obtained with the imaging system. Diagnostic yield may be maximized by the use of implanted devices which may be visualized in the image, as a structure distinct from the surrounding tissue, without affecting the image quality of the surrounding tissue structures.

The verb "degrade" (or another form of this verb) will sometimes be used herein, including in the claims, to refer collectively to the corresponding form of the verbs "distort" and "obscure."

In addition to such medical applications of interventional imaging, it may also be commercially or scientifically useful to employ a tool (not necessarily a medical instrument) to perform an operation (other than medical therapy) on a target (not necessarily a human patient) in the imaging region of an imaging system. Ideally, the tool would not distort or degrade the images obtained. In addition, the tool may be designed in such a way that the images show both the target and the tool during the operation.

In medical diagnosis or therapy using an imaging procedure, the target is all or part of a human patient or animal positioned in the imaging region of an imaging system (where "imaging region" denotes the space within an imaging system in which a target can be imaged), and the imaging system produces an image of one or more selected portions of the patient.

In the following discussion and description of the invention, magnetic resonance imaging ("MRI") is used as a representative example of an imaging modality which is useful during interventional procedures. The reliance on MRI as an example is not intended to imply that the devices of the invention are exclusively useful with MRI. Similarly, for clarity and brevity, a single device of the invention, namely a biopsy needle, will form the basis of the succeeding discussion. However, it will be appreciated by those of ordinary skill in the art that devices of the invention, beyond the described biopsy needle, will find application in interventional procedures using MRI and imaging modalities other than MRI.

Magnetic resonance imaging ("MRI") systems are in widespread use for medical diagnosis. However, new applications including therapy, as well as other applications are being developed. Medical interventional procedures (e.g., therapy or invasive diagnostic procedures) performed on a target (i.e., a patient) while the target is being imaged using MRI is sometimes referred to as interventional magnetic resonance (or "magnetic resonance therapy" or "MRT"), as explained in Jolesz, Ferenc A., Blumenfeld, Morry S., "Interventional Use of Magnetic Resonance Imaging," Magnetic Resonance Quarterly, Vol. 10, No. 2, pp. 85–96 (Jolesz, et al.). Throughout this specification and in the claims, MRT is used in a broad sense to denote both diagnostic and therapeutic applications of interventional MRI. However, it is understood that other imaging modalities can be used to guide therapeutic procedures.

During magnetic resonance imaging, an MRI system generates a strong magnetic field. When a target object (containing water molecules or other hydrogenous compounds) is positioned in the field, the field aligns the magnetic dipoles of the hydrogen nuclei within the water or other molecules, as explained for example in Morris, Peter G., Nuclear Magnetic Resonance Imaging in Medicine and Biology, Clarendon, Oxford, 1986. The magnetic field strength required to so align the magnetic dipoles is typically on the order of one Tesla, but field strengths significantly higher and lower than one Tesla are also used in various applications of MRI. The magnetic field imparts a resonant frequency to the nuclei that is proportional to the field strength. Once aligned by the magnetic field, the magnetic dipoles in the tissue at a prescribed location can be energized by application of radio frequency (RF) energy at the resonant frequency determined by the magnetic field at the prescribed location. Following excitation of the tissue sample by an RF pulse, the RF pulse is turned off and the stored electromagnetic energy in the tissue is emitted by the resonating magnetic dipoles (i.e., the protons spinning at their resonance frequency). Imaging occurs as a result of detecting stored energy as it is emitted from each of many different regions within the target.

In MRT, both the target and the interventional instrument will be affected by the applied magnetic field and the RF pulse.

Throughout this specification, including in the claims, the term "instrument" is used in a broad sense to denote any tool, instrument, or other object employed to perform (or useful for performing) an operation (such as but not limited to medical therapy) on a target, or a device which is implanted in the body for some therapeutic reason or purpose. If the instrument embodies the invention it will not significantly distort or degrade the images obtained with the imaging system. Further, instruments embodying the invention may appear on the target images produced by the MRI system.

The term "target" denotes any object to be imaged by the MRI system (such as but not limited to a human patient). Typically, the structure of a "target" is not specially designed or altered to enhance or optimize visibility when imaged by an MRI system. In contrast, the structure of the inventive "instrument" is specially designed to be visible while creating minimal or no artifacts on MR images.

Throughout this specification, including in the claims, the expression "MR image" denotes a magnetic resonance image (typically displayed on a display device such as a cathode ray tube or flat panel display) generated by an MRI system of whatever object is (or whatever objects are) present in a selected cross-section of its imaging region. It is intended that an MR image is used as a representative example of the diagnostic output of an imaging modality. The present invention is understood to be generally useful in other forms of interventional diagnostic imaging as well.

To appreciate one important class of medical uses of instruments designed in accordance with the invention, the following background considerations are helpful.

One of the most promising opportunities for cost reduction in the medical field is more widespread use of image guided "minimally invasive" therapy. The term "minimally invasive" refers to the fact that the patient is not traumatized by radical surgical openings to access diseased tissue. Conventional invasive surgery is typically associated with a higher risk of complications than is minimally invasive surgery, and usually requires longer periods of hospitalization.

One of the most promising imaging modalities for minimally invasive therapy is magnetic resonance imaging ("MRI"). This is because MRI gives superior soft tissue contrast that clearly images important anatomical features, allowing identification of normal versus abnormal tissue structures. However, it will appreciated by those of skill in the art that other interventional diagnostic modalities such as X-Ray computed tomography (i.e., "CT"), ultrasonography, fluoroscopy, and so on, may afford an acceptable diagnostic yield. Thus, minimally invasive therapy is not constrained to being performed solely in conjunction with MRI.

Principal manufacturers of MRI equipment have developed new generations of high-speed MRI systems which permit continuous, real time visualization of tissue during surgical and endovascular procedures. Such recently developed MRI systems also provide better access to the patient. In one recently developed class of MRI systems, the patient is supported on a table between two large, doughnut-shaped magnets. With a magnetic field set up between the magnets, real time images ("MR images") are produced on a monitor above the patient. This provides a surgeon with physical access to the patient, and enables the surgeon to perform a procedure on the patient while viewing on the monitor in real time the internal tissue structures which are the object of the procedure. AS MRI technology develops, the clarity, definition, and variety of images available to surgeons are expected to improve significantly (as discussed in Jolesz, et al.).

In MRI, the presence of both the magnetic and RF fields used in the imaging process place several constraints on each instrument to be positioned or manipulated near or in the imaging region of the MRI system, including the following:

1. the instrument must be essentially non-ferromagnetic, so that it is not attracted by the magnetic field (such attraction would create a safety problem). This consideration applies to any object which is used near (or which is inserted into or implanted within) the patient being imaged, because the magnetic field would subject such an object or implant to undesirable forces and torques if it were made entirely or partially of ferromagnetic material;

2. an electrical instrument must be tolerant of the static and pulsed magnetic and RF fields, in the sense that it can function in the presence of these fields;

3. an implant or instrument should not be subject to significant induction heating due to the applied RF field; and 4. the instrument should not create imaging artifacts that obscure or distort the image of the target. This final constraint is generally true of instruments to be used with any diagnostic imaging modality.

Because of these constraints, instruments used in MRT operations have conventionally been made of non-ferromagnetic metal such as titanium, nitinol, some types of stainless steel, aluminum, copper, brass, etc. However, such non-ferromagnetic metal instruments have the following imaging property when imaged together with a human patient in an MRI system. The non-ferromagnetic metal instruments, just as most non-hydrogenous materials, will be "negatively" imaged by the MRI system as a black void in a positive background (a "sea" of gray shaded tissue structures). The instrument displaces tissue that normally would be imaged. Although such voids are easily visualized in regions of tissue of high signal intensity, in areas where the patient's tissue has a dark gray or black appearance (due to a weak or absent signal from the magnetic dipoles of its water molecules), the negative image (void) created by the instrument may be insufficient for visualization.

Also, many materials, even if they are non-ferromagnetic can cause two kinds of imaging artifacts that distort the image in the region adjacent to the instrument. The first is a magnetic susceptibility artifact which is caused by the difference in magnitude between the magnetic susceptibility of tissue and that of the instrument material. This difference causes the magnetic field around the instrument to be distorted thus causing an artifact. This type of artifact will frequently be seen as an image void around the instrument which is many times its normal dimension (Moscatel, M. A. et. al., "Biopsy Needles and Devices: Assessment of Ferromagnetism and Artifacts during Exposure to a 1.5T MR System", Journal of Magnetic Resonance Imaging 1995;5:369–372). The second type of artifact is the eddy current artifact which is caused by eddy currents in electrically conducting material. They exist because an electrically conducting material acts like an antenna in the presence of the applied radio frequency energy in the MR system thus causing eddy currents to flow in the surface of the conductor. These eddy currents, in turn, create their own local magnetic field which distorts the imaging field thus creating an imaging artifact (Camacho, C. R., et. al. "Nonsusceptibility Artifacts Due To Metallic Objects in MR Imaging"; Journal of Magnetic Resonance Imaging 1995;5:75–88).

To obtain the nearly real-time MR images which are necessary for MR-guided interventional procedures, fast imaging sequences such as gradient-echo imaging techniques are currently the modality of choice. However, these fast imaging sequences are prone to generating debilitating image artifacts when used in conjunction with metallic devices. Due to the increased T2 sensitivity of gradient refocusing (echo) techniques, these fast imaging sequences tend to accentuate the magnetic susceptibility artifacts arising from metallic instruments within the imaging field.

It would be desirable to have available instruments for use in an MRI or other imaging system which did not generate artifacts or otherwise distort or diminish the quality of the image.

Attempts to design such "MRI compatible" instruments have relied on the use of non-ferromagnetic metal alloys. For example, Lufkin and coworkers have demonstrated the use of a needle made of high nickel content stainless steel for MR-guided aspiration cytology. Lufkin, R., Teresi, L., Hanafee, W. "New Needle for MR-Guided Aspiration cytology of the Head and Neck," American Journal of Roentgenology, 149:380–382 (1987). The new needle showed fewer artifacts when used in slower imaging sequences than did prior art needles made of a stainless steel with a lower nickel content. However, in rapid imaging sequences, the number of artifacts increased dramatically. Of particular note was the presence of a sphere- or dumbbell-shaped artifact at the needle's tip. Such an artifact tends to obscure the true position of the needle tip. In general, the shape and size of such an artifact are also dependent on the orientation of the instrument with respect to the magnetic field.

In addition to instruments which are compatible with the conditions necessary for fast MR image acquisition, it would be desirable to have available an instrument for use in an MRI system which was "MR visible," in the sense that the instrument would have its own identifiable magnetic resonance signal (and thus be positively imaged) in the presence of the combined magnetic and RF fields of the MRI system.

There have been attempts to design such an "MR visible" instrument. For example, U.S. Pat. No. 4,989,608, issued Feb. 5, 1991 to Ratner, and U.S. Pat. No. 5,154,179, issued Oct. 13, 1992 to Ratner, disclose flexible catheters which are intended to be MR visible. In some embodiments, the flexible catheters are composed of plastic, and ferromagnetic particles are distributed uniformly throughout the volume of each catheter or in patterned regions within each catheter's volume (e.g., in stripes along each catheter's longitudinal axis). In other embodiments, the catheters are manufactured to include one or more internal lumens filled with liquid (containing aqueous paramagnetic ions). Each lumen runs the entire length of the device and is an integral and nonremovable portion of the catheter structure.

A disadvantage of the Ratner method is that the ferromagnetic particles or aqueous paramagnetic ions must be immersed in a carrier volume of material. This carrier volume must be either the volume of the plastic catheter material itself or a liquid volume which is inserted in a catheter lumen. Further, the Ratner method does not afford the opportunity to specifically visualize a region of the instrument using a removable marked element, and then removing the marked element from the instrument, to enable performance of a medical interventional procedure.

U.S. Pat. Nos. 4,989,608 and 5,154,179 also teach that "non-ferrous materials" can be included in a flexible catheter containing embedded ferromagnetic particles.

The Ratner references do not suggest the use of a rigid carbon-fiber material to manufacture the body of a medical invasive instrument, nor do they suggest the use of a carbon-fiber instrument in either the presence or the absence of a contrast agent. Additionally, a lumen filled with a liquid contrast agent as taught by Ratner runs the length of an instrument and forms an integral portion of the body of the instrument. The prior art is believed to include no suggestion to use a removable contrast agent-containing element (e.g., a rigid stylet) which is removable from the remaining portion of an instrument. In accordance with the invention, such a stylet can be inserted into the carbon-fiber body of a device to impart additional rigidity to the device and MR conspicuity to an operative portion of the device. In accordance with the present invention, subsequent to aligning the operative portion of the device within the desired region of the target, the stylet can be removed and, if desired, the stylet can be replaced with another second component of the instrument.

One embodiment of the present invention is based on the inventor's recognition that medical invasive devices made of a carbon-fiber composite material (which has very low electrical conductivity) are virtually artifact-free on MR images. A second embodiment is based on the recognition that removable portion of a carbon-fiber instrument can be marked with a contrast agent, and removably positioned with respect to the instrument to impart conspicuity to a desired portion of the instrument. The fact that MR contrast agents will show up in a MR image when they are inside a carbon fiber enclosure is an important discovery by the inventor. This means that carbon fiber is sufficiently transparent to RF energy so imaging of the contrast agent can occur. The inventor has recognized that the combination of structural rigidity, strength and RF transparency of carbon-fiber composite material make such material an ideal candidate for forming biopsy needles and other invasive instruments and devices. Neither of the above-cited Ratner patents suggests that the instrument material containing the MR contrast agent must be transparent to radio frequency energy in order for a contrast agent to be made visible in the MR image. Metallic materials such as titanium and other non-ferrous alloys that are electrically conductive and enclose a contrast agent would shield the contrast agent from the RF energy (by the well known Faraday shielding effect) and render the contrast agent useless as a conspicuity device.

SUMMARY OF THE INVENTION

In a class of embodiments, the invention is a medical invasive instrument for use in an MRI or other imaging system. The instrument has a rigid body made of a carbon-fiber (or glass-fiber) composite material. When in use in an imaging system, the instrument does not unacceptably obscure or distort the image of a target (e.g., a typical target, such as human tissue, adjacent to the instrument) in any of the images of the target (where both the instrument and target are in the imaging system's imaging region when the imaging system produces images of the target).

In another class of embodiments, the invention is a medical invasive instrument for use in an MRI or other imaging system, wherein an operative or other portion of the instrument is marked with a contrast agent which is appropriate to the imaging modality, and all (or substantially all) of the remaining portion of the instrument is made of carbon-fiber (or glass-fiber) composite material. In such embodiments, during an imaging procedure, the visibility of the marked portion of the instrument is conspicuously enhanced relative to that portion of the instrument which is not marked with a contrast agent.

In preferred embodiments, an auxiliary portion of the instrument contains (or is otherwise marked with) a contrast agent which is appropriate to the imaging modality, and all (or substantially all) of the remaining portion of the instrument is made of carbon-fiber composite, glass-fiber composite, or zirconia ceramic material. The auxiliary portion is designed to be removed after the instrument has been positioned within the target, and optionally replaced by a substitute portion. In embodiments which are essentially tubular instruments (e.g., catheters or biopsy needles) the marked portion of the device can be a marker stylet or other rigid member which contains or is otherwise marked with a contrast agent and which fits removably inside a central channel of the device. The stylet (or other rigid member) is preferably made of carbon-fiber composite material and serves to impart additional rigidity to the tubular instrument as well as to mark a desired portion of the device with a contrast agent.

In alternative embodiments (e.g., forceps, retractors, or other instruments shaped such that they are unsuitable for use with a removable tubular stylet), the contrast agent can be encapsulated within the instrument in a chamber (e.g., a chamber between sections of the body of the device). Alternatively, the device can be manufactured to include one or more exterior pouches for containing the contrast agent.

In some preferred embodiments, the contrast agent is an aqueous solution of a paramagnetic metal ion. In other preferred embodiments, the contrast agent is an organic chelate of a paramagnetic metal ion (e.g., an organic chelate of gadolinium III). When the instrument is to be imaged using MRI, the contrast agent should consist of a material in which the proton concentration per unit volume is substantially greater than the proton concentration in the target material. Since MR signal intensity is partially dependent on proton density, regions of high proton density will give rise to a signal of higher intensity than regions with a lower proton density. In other preferred embodiments, the contrast agent is an iodinated organic compound. In further preferred embodiments, the contrast agent is a solution comprising microbubbles of air or another gas, or the marked portion of the device (sometimes referred to as a "contrast region") contains an air-filled void.

Another aspect of the invention is an imaging method including the steps of positioning both a contrast agent-marked instrument (constructed in accordance with the invention) and a target in the imaging region of an imaging system, and operating the system to produce an image showing both the target and the instrument, preferably while performing a medical interventional procedure on the target using the instrument.

DETAILED DESCRIPTION OF THE PREFERRED EMBODIMENTS

The expressions "carbon-fiber material" and "carbon-fiber composite material" are used interchangeably herein to denote a carbon-fiber (or graphite-fiber) reinforced composite material. An example of such a material is a fabric (or array of filaments) of carbon-fiber and a polymeric matrix material. Typical carbon-fiber material used in preferred embodiments of the invention has very low electrical conductivity and is highly anisotropic (which properties minimize problems with eddy currents when the carbon-fiber material is used in a MRI system). Where the carbon-fiber material is to be used in a MRI system, it should be non-ferromagnetic (so that it will not be subjected to undesirably strong magnetic forces while undergoing MR imaging).

The expressions "glass-fiber material" and "glass-fiber composite material" are used interchangeably herein to denote a glass-fiber reinforced composite material. Typically, glass-fiber composite material has less rigidity than carbon-fiber composite material. However, glass-fiber composite material can have sufficient rigidity to implement embodiments of the inventive instrument useful for some applications.

The expressions "zirconia," "zirconia ceramic," and "zirconia ceramic material" are used interchangeably herein to denote either stabilized zirconia (zirconium dioxide) or a ceramic material that consists primarily of stabilized zirconia. Zirconia is RF transparent (i.e., it is transparent at radio frequencies) and can be used with a Gadolinium contrast agent of the type described herein. Typical zirconia material has high strength but is brittle.

Figure 1:
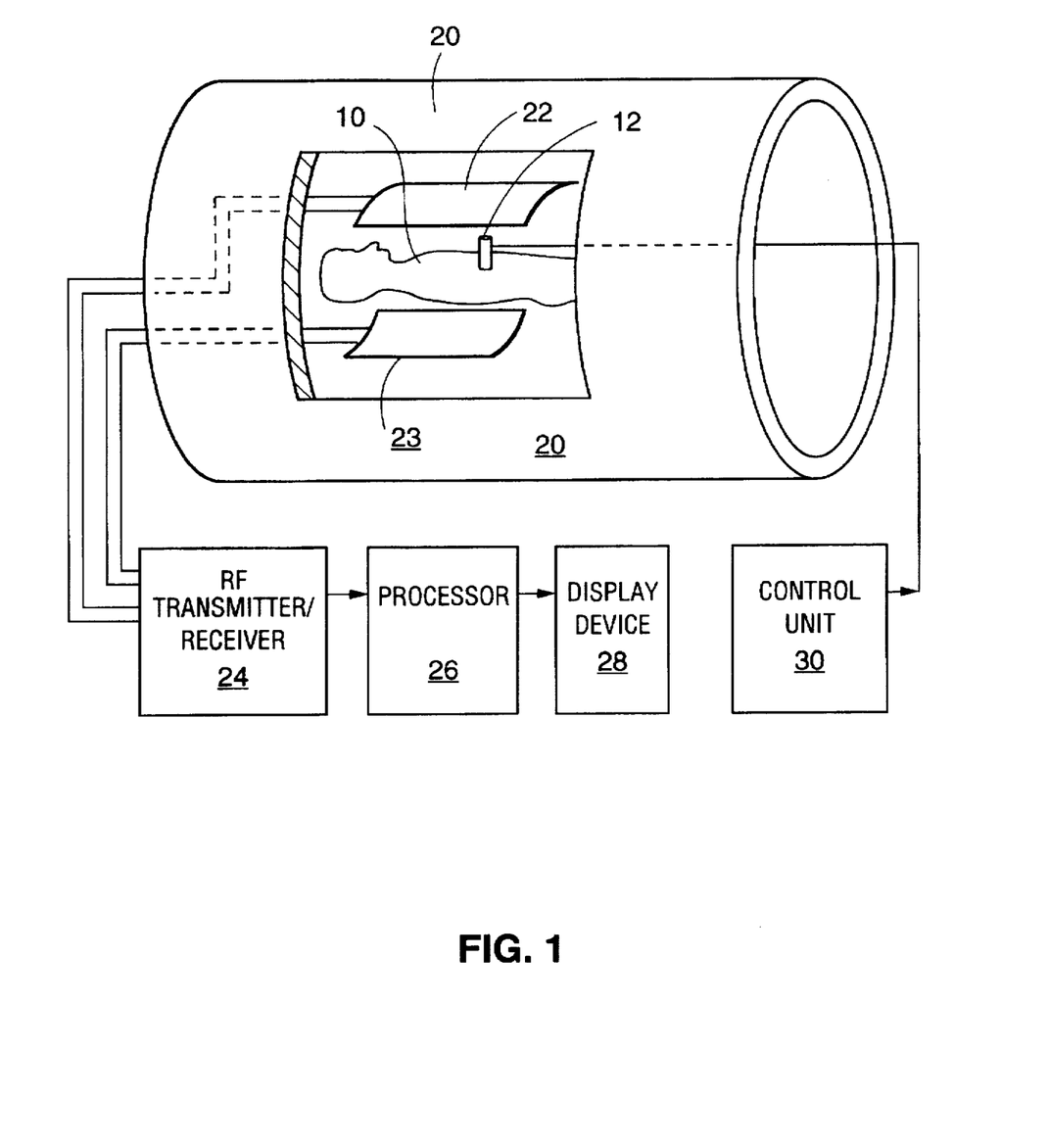
FIG. 1 is a simplified schematic diagram of an MRI system with an embodiment of the instrument of the invention, and a target, in its imaging region.

The MRI system shown in FIG. 1 can be operated to implement the magnetic resonance imaging method of the invention. With reference to FIG. 1, magnet structure 20 includes magnets for producing a magnetic field suitable for magnetic resonance imaging of target 10. A portion of structure 20 is cut away in FIG. 1 to show both target 10 and instrument 12 positioned in an imaging region which lies between coils 22 and 23 and is surrounded radially by structure 20. An RF transmitter within RF transmitter/receiver 24 supplies an appropriate electric signal to coils 22 and 23 to cause an RF magnetic field to be superimposed with the magnetic field (due to magnet structure) in the imaging region. The superimposed magnetic and RF fields causes magnetic dipoles of target 10 to resonate. An RF receiver within transmitter/receiver 24 detects electromagnetic radiation that has propagated from the resonating magnetic dipoles in target 10 to coils 22 and 23. Unit 24 supplies signals indicative of the detected radiation to processor 26 (preferably a programmed digital computer), and processor 26 processes these signals to generate display data (for determining an MR image) and supplies the display data to display device 28 (which can be a conventional cathode ray tube or flat panel display device). In response to the display data, an MR image of a selected cross-sectional portion of target 10, or a selected cross-sectional portion of target 10 including instrument 12, is displayed on display device 28. Instrument 12 is a medical interventional instrument designed in accordance with the invention.

In preferred embodiments, target 10 is a human patient or animal and instrument 12 is a medical device such as a scalpel, forceps, retractor, biopsy needle, catheter, or the like.

While viewing the MR image on display device 28, a medical practitioner can manipulate instrument 12. The practitioner may accomplish this manipulation manually (e.g., by gripping and moving the instrument). Alternatively, instrument 12 can be manipulated remotely in response to instrument control signals which are generated by instrument control unit 30 (in response to a medical practitioner's actuation of controls of unit 30) and supplied to from unit 30 to instrument 12.

Figure 2:
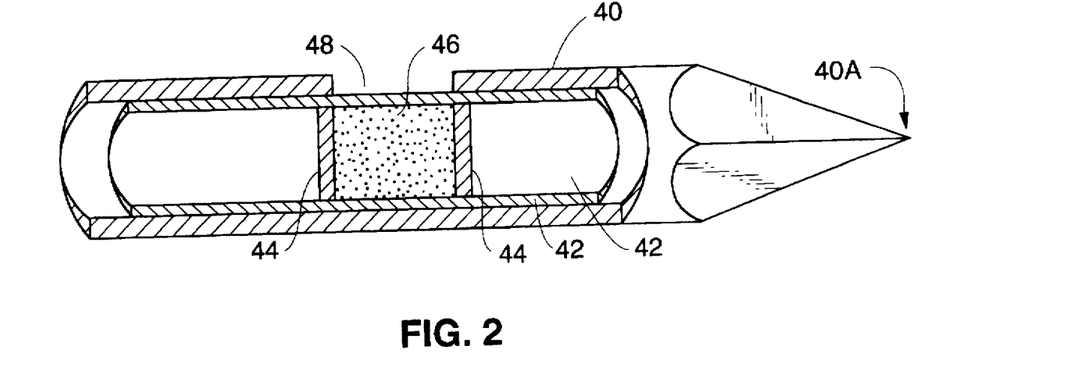
FIG. 2 is an enlarged, simplified cross-sectional view of an embodiment of the inventive carbon-fiber composite (or glass-fiber composite, or zirconia ceramic) biopsy needle, including a contrast media-containing marker stylet within it.

One embodiment of the invention, suitable for use as instrument 12 in the FIG. 1 system, is the hollow needle-shaped device shown in FIG. 2 which includes a generally cylindrical body 40 which has a sharp tip 40A at its distal end. Body 40 is preferably composed of a carbon-fiber composite material, but alternatively is composed of glass-fiber composite material or zirconia material.

Figure 6:
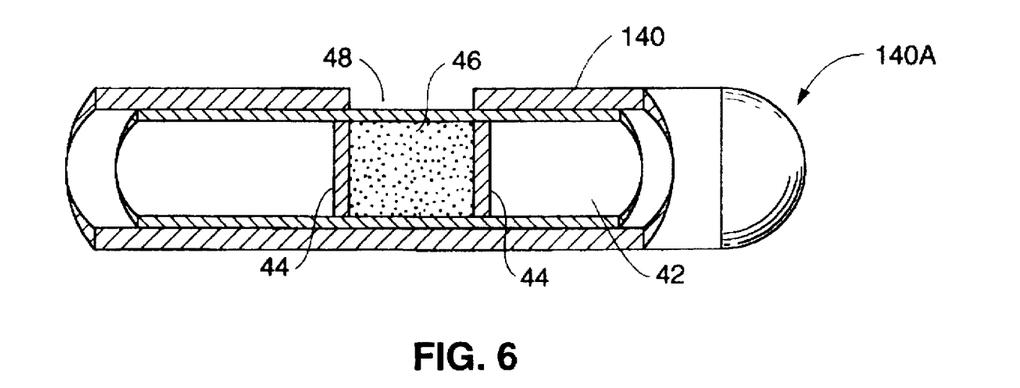
FIG. 6 is an enlarged, simplified cross-sectional view of a blunt-tipped embodiment of the inventive biopsy needle (made of carbon-fiber composite, glass-fiber composite, or zirconia ceramic), including a contrast media-containing marker stylet within it.

Another embodiment of the invention, suitable for use as instrument 12 in the FIG. 1 system, is the hollow needle-shaped device shown in FIG. 6 which includes a generally cylindrical body 140 which has a blunt tip 140A at its distal end. Body 140 is preferably composed of a carbon-fiber composite material, but alternatively is composed of glass-fiber composite material or zirconia material. The identically numbered elements of the FIG. 2 and FIG. 6 embodiment are identical.

With reference again to FIG. 2, a marker stylet 42 is removably positioned within the central chamber of the body 40 (which extends along the longitudinal axis of body 40), with its longitudinal axis parallel to that of body 40. Marker stylet 42 contains a contrast agent 46 which is encapsulated in a chamber formed by the inner cylindrical surface of the marker stylet and two bulkheads 44 oriented perpendicularly to the longitudinal axis of stylet 42. Body 40 has an orifice 48 (referred to as a tissue collection recess or tissue collection orifice) which extends through its cylindrical side wall. The contrast agent chamber is positioned within marker stylet 42 such that, during imaging with the stylet fully extended distally within body 40 (as shown in FIG. 2), the image of the contrast agent 46 determines the location of tissue collection recess 48, and the image of the contrast agent 46 is specifically enhanced relative to that of the rest of the device.

Body 40, stylet 42, and barriers 44 (but not marker 46) are preferably made of carbon-fiber material (but alternatively are composed of glass-fiber composite or zirconia material). In a preferred embodiment, components 40, 42, and 44 are constructed of a carbon-fiber material which is substantially rigid. Substantially rigid is defined herein as exhibiting sufficient rigidity to penetrate mammalian tissue without significant bending or deforming. A particularly useful material for practicing the invention is a braided carbon-fiber material such as that available through Polygon Corp. of Walkerton, Ind.

Preferably, contrast agent 46 consists of a fluid which is either a pure compound or a solution of a compound in an appropriate solvent. In an embodiment for use with MR imaging, contrast agent 46 can be a paramagnetic ion, organic chelate of a paramagnetic ion or a material with a higher proton density than that of the material of the target to be imaged with the instrument inserted therein. In an embodiment for use in an x-ray system (e.g., a CT or fluoroscopy system) the contrast agent can be an x-ray opaque agent such as an iodinated hydrocarbon or heavy metal such as barium. In a further embodiment for use in conjunction with ultrasonography, contrast agent 46 may be an air void or a solution containing microbubbles of a gas or other agent having an acoustic impedance mismatch relative to the material of the target. When used in conjunction with positron emission tomography (PET), contrast agent 46 can be an agent which emits positrons during the course of the imaging procedure.

In embodiments utilizing solutions of one or more contrast agents, the solutions should be of a concentration sufficient to impart conspicuity to the marked instrument portion, and yet not so concentrated as to give rise to artifacts which would defeat the purpose of the invention. For similar reasons, those embodiments using pure materials as contrast agents should be constructed so as to limit the volume of each contrast agent-containing chamber or pouch (or other marked region) and thus to limit the amount of contrast agent contained by the instrument to prevent imaging artifacts.

Figure 3:
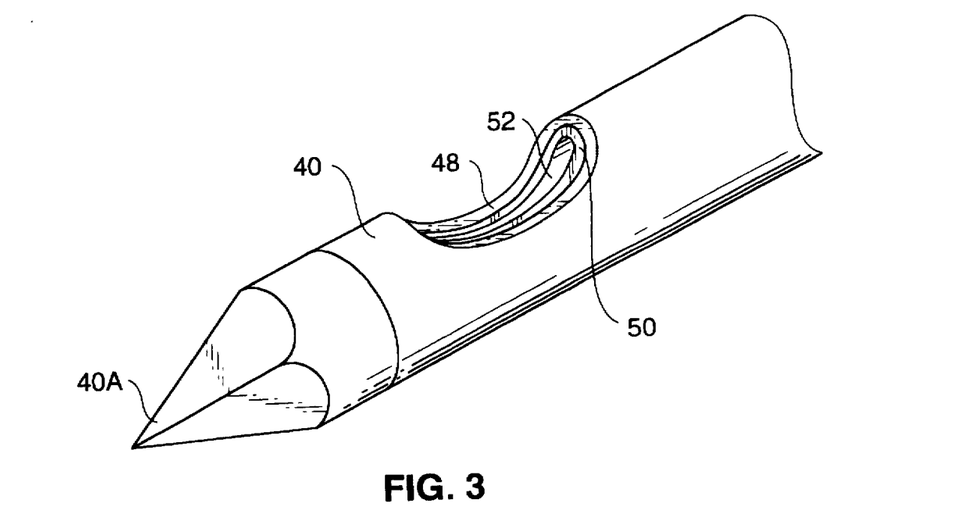
FIG. 3 is a simplified view of an assembled side-cutting biopsy needle (made of carbon-fiber composite, glass-fiber composite, or zirconia ceramic) showing the relationship of the tissue collection recess of the outer cannula and the tissue collection recess of the inner obturator.
Figure 4A:
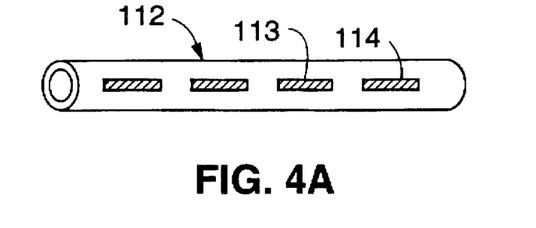
FIGS. 4(a), 4(b), 4(c), 4(d), 4(e), and 4(f) are examples of portions of instruments having different contrast agent patterns that are used in alternative embodiments of the invention. (In those patterns consisting of discrete elements, such as that of FIG. 4(c), each element can have a different volume or concentration of contrast agent).
Figure 4B:
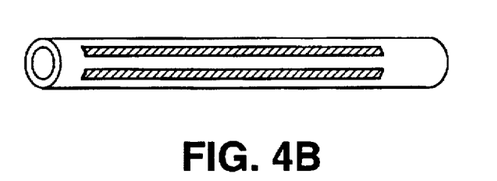
Figure 4C:
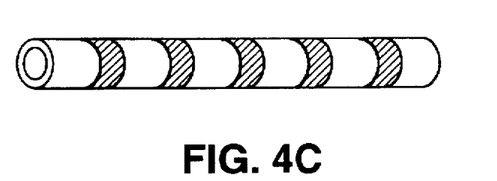
Figure 4D:
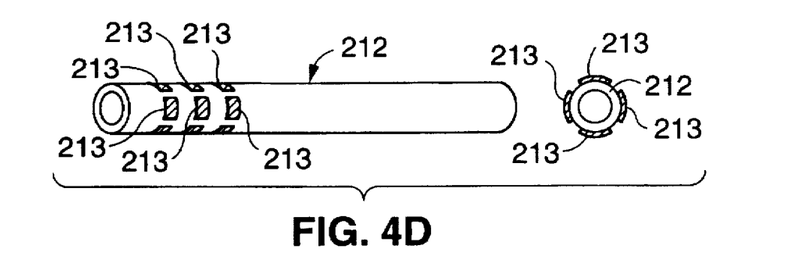
Figure 4E:
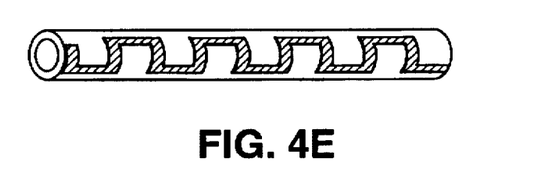
Figure 4F:
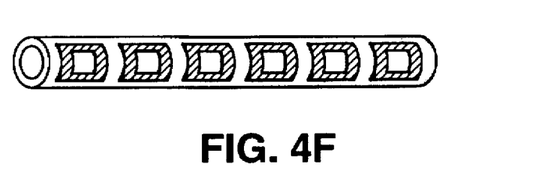

Another embodiment of the instrument of the invention is shown in FIG. 3. The instrument of FIG. 3 is a fully assembled, sharp-tipped biopsy needle, which is preferably composed of a carbon-fiber composite material, but alternatively is composed of glass-fiber composite material or zirconia material. As can be seen in FIG. 3, the biopsy needle of FIG. 3 consists of two components: outer cannula 40 and inner obturator 50. Outer cannula 40 has a sharp tip 40A and a tissue collection recess 48 which opens into the interior of the cannula. Outer cannula 40 can be identical to body 40 of FIG. 2, but inner cannula 50 is different than (and is intended to replace) stylet 42 of FIG. 2. Inner obturator 50 also has a tissue collection recess 52. Accurate insertion and location of the recesses 48 and 52 relative to the target tissue or lesion to be biopsied is critical. Therefore to mark the exact location of tissue collection recess 48, obturator 50 is removed and marker stylet 42 is inserted. Under MR image guidance, the biopsy needle body 40 with marker stylet 42 (as shown in FIG. 2) is inserted into the tissue or lesion to be biopsied. When MR imaging confirms that the biopsy needle is placed properly, marker stylet 42 is replaced with obturator 50 without disturbing the location of body 40 and tissue collection recess 48. When recesses 48 and 52 are aligned (as shown in FIG. 3), the interior of the device is in fluid communication with the exterior of the device. A pump or other device (not shown) is provided for applying a vacuum to the interior of the biopsy needle, thereby drawing a tissue or lesion sample through the aligned recess into the interior of the device. The inner obturator 50 is then rotated (about its longitudinal axis) relative to outer obturator 40, thus excising (shearing) the tissue sample and causing it to be retained within the device.

Figure 7:
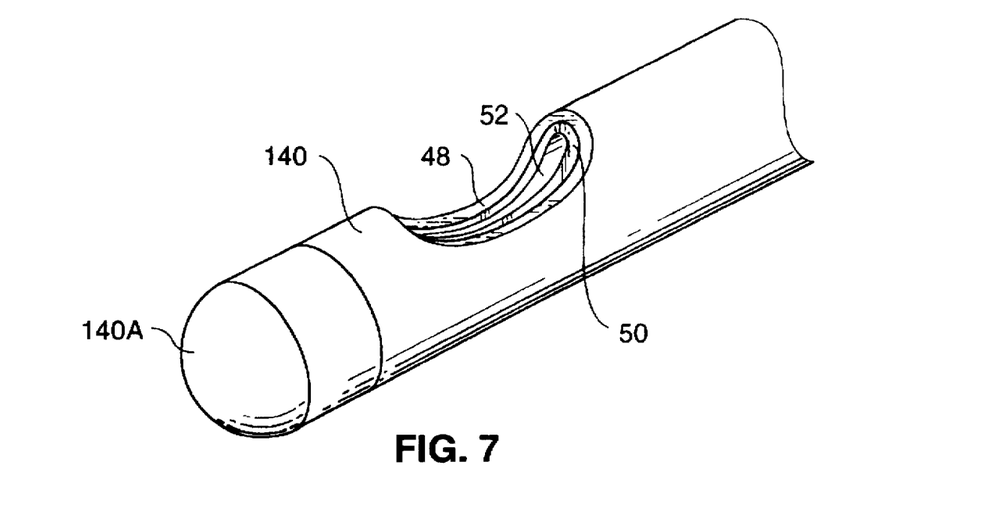
FIG. 7 is a simplified view of an assembled embodiment of an inventive side-cutting biopsy needle (having a blunt tip) showing the relationship of the tissue collection recess of the outer cannula and the tissue collection recess of the inner obturator.

Another embodiment of the instrument of the invention is shown in FIG. 7. The instrument of FIG. 7 is a fully assembled, blunt-tipped biopsy needle (having outer cannula 140 with blunt tip 140A, but otherwise identical with the FIG. 3 embodiment). The instrument of FIG. 7 is preferably composed of a carbon-fiber composite material, but alternatively is composed of glass-fiber composite material or zirconia material.

Figure 8:
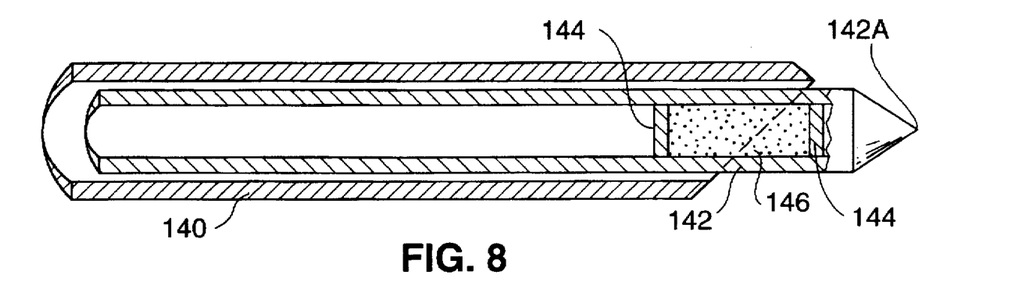
FIG. 8 is an enlarged, simplified cross-sectional view of a thrusting biopsy needle in accordance with the invention, including a cannula (made of carbon-fiber composite, glass-fiber composite, or zirconia ceramic) and a contrast media-containing marker stylet within the cannula.

Another class of embodiments of the invention will be described with reference to FIGS. 8, 9, and 10. Each such embodiment is a thrusting biopsy needle, including cannula 140 made of substantially rigid material (which is preferably made of a carbon-fiber composite, but which is alternatively made of a glass-fiber composite, or zirconia ceramic). As shown in FIG. 8, a contrast media-containing marker stylet 142 (having a sharp distal end 142A) is disposed within cannula 140. Marker stylet 142 contains a contrast agent 146 which is encapsulated in a chamber formed by the inner cylindrical surface of the marker stylet and two bulkheads 144 oriented perpendicularly to stylet 142's longitudinal axis (the horizontal axis in FIG. 8). Preferably, agent 146 is a Gadolinium contrast agent (e.g., a solution of Gd-DTPA). The sharp distal end 142A of stylet extends beyond the distal end of cannula 140. In use, stylet 142 and cannula are fixedly attached together (in the relative position shown in FIG. 8) and are advanced in a distal direction (e.g., toward the right in FIG. 8) into a target (i.e., a patient from whom a biopsy sample is to be taken), while assembly is imaged together with the sample (using an MRI system or other medical imaging system).

Stylet 142 (including barriers 144 but excluding contrast agent 146) is made of substantially rigid material (preferably a carbon-fiber composite material, but which can alternatively be a glass-fiber composite or zirconia ceramic material). Since both stylet 142 and cannula 140 are made of carbon-fiber composite (or glass-fiber composite or zirconia ceramic) material, the contrast agent 146 is positively imaged by the medical imaging system but the FIG. 8 assembly does not distort or obscure the image of the target also being imaged by the medical imaging system.

During the described imaging step, agent 146 (and thus cannula 140, which is in a known, fixed position relative to agent 146) is positioned in a desired position in the target. Then, stylet 146 is removed from within cannula 140 and stylet 146 is replaced by sample obturator 152. Obturator 152 is spring-loaded by a conventional spring assembly (not shown in FIG. 9) in a fixed, extended position relative to cannula 140 (as shown in FIG. 9). An orifice 153 (referred to as a tissue collection recess or tissue collection orifice) extends through the cylindrical side wall of obturator 152.

Figure 9:
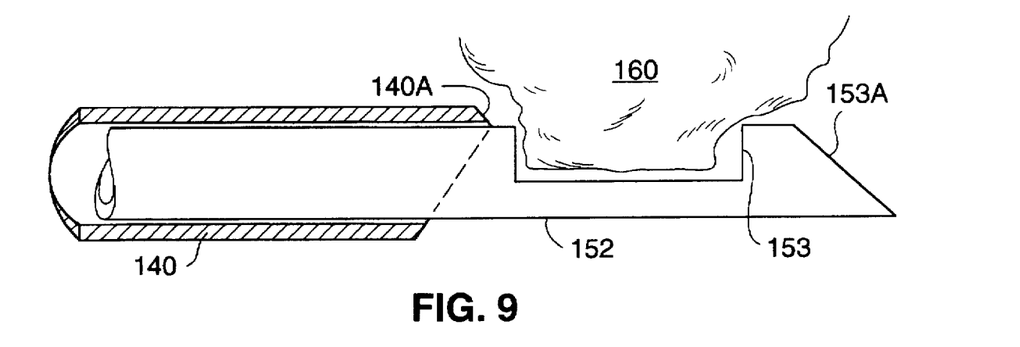
FIG. 9 is an enlarged, simplified cross-sectional view of the cannula of FIG. 8, and a sample obturator (instead of the stylet) within the cannula. The obturator is in an extended position relative to the cannula.

In the extended position shown in FIG. 9, both distal end 153A and orifice 153 of obturator 152 extend beyond the distal end of cannula 140 into target 160 (target 160 is typically a tissue mass to be biopsied). A pump or other device (not shown), provided for applying a vacuum to the interior of obturator 152, is operated to cause a sample of the target 160 to be drawn through tissue collection orifice 153 into the interior of obturator 152 (as shown in FIG. 9).

Figure 10:
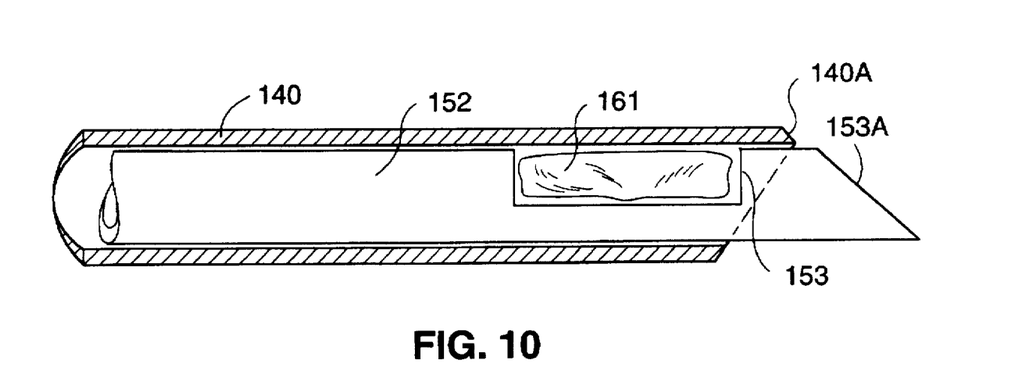
FIG. 10 is an enlarged, simplified cross-sectional view of the cannula and sample obturator of FIG. 9, with the obturator in a retracted position relative to the cannula.

Then, the spring assembly is released (in a conventional manner) to retract obturator 152 relative to cannula 140 in the proximal direction (the direction opposite to the distal direction) into the retracted position shown in FIG. 10. During this retraction step, obturator 152 pulls a portion of target 160 in the proximal direction, and distal end 140A of cannula 140 shears off a sample 161 of the target 160. Sample 161 remains within obturator 152 (as shown in FIG. 10) while the entire biopsy needle apparatus is withdrawn from the target.

In another class of embodiments, the instrument of the invention includes a carbon-fiber composite (or glass-fiber composite) body and a contrast agent which is contained in or on a patterned region of the body (but not the entire body). The patterns are designed to further enhance and control the visibility of instrument. The geometry of such patterns needed to control the visibility may be dependent on the surface geometry of the instrument and on the polarization of the RF waves used to generate an MR signal in the target (e.g., target 10 of FIG. 1). Examples of portions of instruments, each having such a patterned region, are shown in FIGS. 4(a)–4(f). In those patterns consisting of discrete elements (such as that of FIG. 4(a) or FIG. 4(c)), each contrast agent containing element can have a different volume or contrast agent concentration. For example, in instrument portion 112 of FIG. 4(a), each of regions 113 and 114 is a volume filled with a contrast agent, whereas the remainder of portion 112 is made of carbon-fiber (or glass-fiber) composite material. Regions 113 and 114 can have the same volume (or different volumes), or the same concentration of contrast agent (or different concentrations of the contrast agent). The contrast agent may be contained within one or more sealed chambers integral to the body of the instrument. Alternatively, the contrast agent may be contained in vials or capillaries which fit on the body of the instrument in a removable fashion. FIG. 4 shows a number of examples of an instrument in the latter class of embodiments. For example, instrument portion 212 of FIG. 4(d) comprises a body of carbon-fiber (or glass-fiber) composite material, and vials 213 of contrast agent mounted on the outer surface of the body.

In preferred embodiments of the contrast marker-containing carbon-fiber (or glass-fiber) composite instrument of the invention, the volume and concentration of the contrast agent is determined experimentally, in the following manner. An MRI system images the instrument several times, while the instrument is inserted in a target (preferably, a typical target such as an MR phantom), each time with a different volume or concentration of contrast agent. The contrast agent volume or concentration which satisfies the following criteria is identified as the preferred volume or concentration: the contrast agent should be plentiful enough to cause the marked portion of the instrument to be positively imaged by the MRI system, and the amount of contrast agent used should not be so great as to cause the instrument to unacceptably distort or obscure the image of the target produced by the MRI system. The instrument is "positively imaged" by the MRI system if a representation of the marked portion of the instrument (which approximates closely the real shape of the marked instrument portion) is visible in an MR image generated by the system, other than as a black or "negative" void in a positive background of gray shaded or colored features. For example, an instrument is minimally "positively imaged" by an MRI system if a gray outline of the instrument's contrast agent-containing region (or a gray shaded region bounded by such an outline) appears in an MR image, together with (but distinguishable from) a gray shaded representation of features of a target.

Figure 5A:
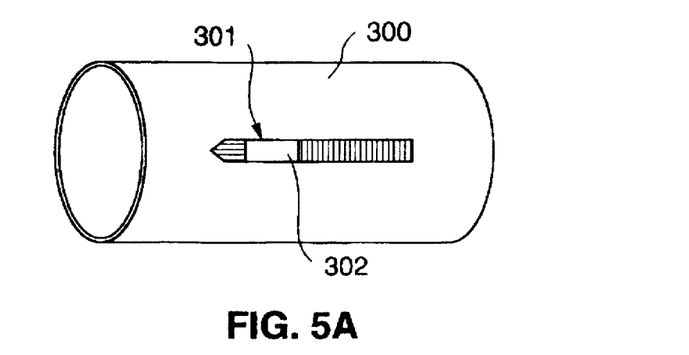
FIG. 5A is a perspective view of an embodiment of the inventive carbon-fiber device which contains the MR contrast agent known as Gd-DTPA in a water phantom.
Figure 5B:
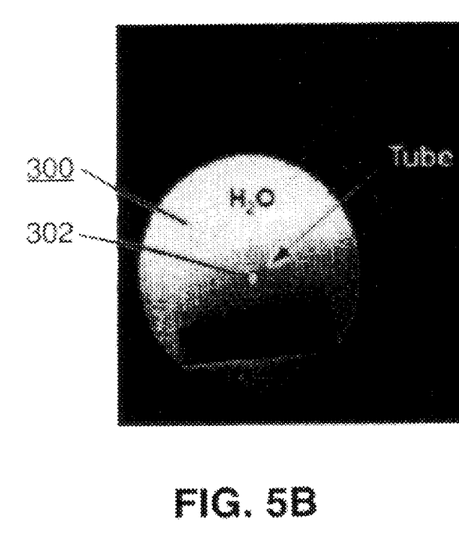
FIGS. 5B and 5C are MR images of the device in the water phantom (FIG. 5B is an end view and FIG. 5C is a side view).
Figure 5C:
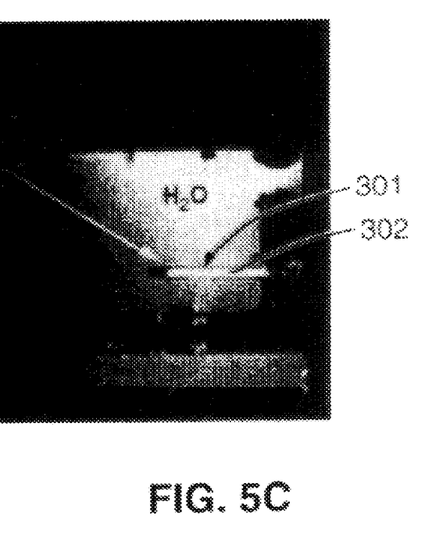

The inventor has obtained experimental data comprising MR images of a tubular body of carbon-fiber (of 0.071 inch outer diameter, with a cylindrical side wall of 0.010 inch thickness) whose interior volume is filled with a Gadolinium contrast agent (a 5 millimolar solution of Gd-DTPA). Images obtained as a result of this experiment are shown in FIGS. 5B and 5C. The Gd-DTPA filled carbon-fiber tube was immersed in a water phantom (as shown in FIG. 5A) and imaged at a field of 2.0 Tesla. The contrast agent filled carbon-fiber body was clearly visible as a region 301 of signal void (representing the unmarked portion of the instrument) surrounding an area of profound signal intensity 302. The region 302 of high signal intensity corresponded to the location of the volume of contrast agent. The image of the water phantom is identified by numeral 300 in FIG. 5B. The data established that the system could generate an MR image that positively showed a region within a carbon fiber body which contained a contrast agent. Importantly, the carbon-fiber material did not shield the contrast media solution from the magnetic or RF fields necessary to generate an MR image of the contrast agent. The inventor has also experimentally shown that the carbon-fiber composite material is x-ray transparent. Thus, under the conditions of an x-ray imaging modality (CT, fluoroscopy, etc.) a tube similarly filled with an appropriate x-ray contrast medium would show a region of profound signal void corresponding to the location of the x-ray opaque contrast medium. Similarly, for ultrasonic imaging an air void or solution of microbubbles in marker stylet 42 has been shown to enhance the ultrasonic image of the needle port (tissue collection recess) 48.

Another aspect of the invention is an imaging method including the steps of positioning both a target and an embodiment of the inventive instrument in the imaging region of an imaging system, and operating the imaging system to produce an image showing both the target and the instrument (preferably while performing a medical interventional procedure using the instrument). It is within the scope of the invention to employ any embodiment of the inventive carbon-fiber (or glass-fiber or zirconia) instrument in performing such a method, including any of the embodiments which contain a region filled with a contrast agent. It is further within the scope of the invention to apply any medical diagnostic imaging modality to generate the image in performing the method of the invention.

Various modifications and variations of the described embodiments of the invention will be apparent to those skilled in the art without departing from the scope and spirit of the invention. Although the invention has been described in connection with specific preferred embodiments, it should be understood that the invention as claimed should not be unduly limited to such specific embodiments.

What is claimed is:

1. An invasive medical instrument for use with a medical imaging system including an imaging region and a means for generating an image of a target object in the imaging region, said image including an image of the target object, said instrument comprising:

an instrument body made of a carbon-fiber composite material, said instrument being sized for use with the target object in the imaging region while said target object is being imaged; and a volume containing a contrast agent contained within or on a portion of the body of the instrument, wherein the instrument also includes a marked element sized for removable insertion within the instrument body, wherein the marked element is made of a carbon-fiber material and the contrast agent is contained within the marked element.

2. A biopsy needle, comprising:

an outer tubular cannula constructed of a substantially rigid material, said cannula having a distal end, a proximal end, a substantially cylindrical wall portion between the distal end and the proximal end, and an axis, wherein the substantially rigid material is a member of the group consisting of carbon-fiber composite material, glass-fiber composite material, and zirconia;

a tissue collection region at the distal end of the outer tubular cannula;

an inner tubular obturator having a distal portion sized for removable insertion within the outer tubular cannula so that the inner tubular obturator is positionable in a selected one of an open orientation and a closed orientation relative to the tissue collection region, where the obturator has a distal end, a proximal end separated from the distal end along an axis, a substantially cylindrical wall portion between the distal end and the proximal end, and a tissue collection orifice extending through the wall portion of said obturator; and a marker stylet having an outer surface, an inner surface, a distal end, and a proximal end separated from the distal end along an axis, the stylet being sized for removable insertion within the outer tubular cannula when the inner tubular obturator is not positioned within said outer tubular cannula, and wherein the stylet has a contrast agent chamber containing a contrast agent.

3. The biopsy needle of claim 2, wherein the marker stylet is made of a carbon-fiber composite material.

4. The biopsy needle of claim 3, wherein the carbon-fiber composite material is a substantially rigid material.

5. The biopsy needle of claim 2, wherein the marker stylet is made of a glass-fiber composite material.

6. The biopsy needle of claim 2, wherein the marker stylet is made of zirconia.

7. The biopsy needle of claim 2, wherein the contrast agent chamber is defined by a distal bulkhead portion of the stylet, a proximal bulkhead portion of the stylet, and a portion of the inner surface of the stylet disposed between the distal bulkhead portion and the proximal bulkhead portion, the contrast agent chamber being positionable adjacent to the tissue collection region of the outer tubular cannula when the stylet is inserted within said outer tubular cannula.

8. The biopsy needle of claim 7, wherein the contrast agent comprises an agent which enhances conspicuity of the contrast agent chamber in images generated by imaging techniques chosen from the group consisting of magnetic resonance imaging, ultrasonography, x-ray, x-ray computed tomography, fluoroscopy, and positron emission tomography.

9. A biopsy needle, comprising:

an outer tubular cannula constructed of a substantially rigid material, said cannula having a distal end, a proximal end, a substantially cylindrical wall portion between the distal end and the proximal end, and an axis, wherein the substantially rigid material is a member of the group consisting of carbon-fiber composite material, glass-fiber composite material, and zirconia;

a tissue collection region at the distal end of the outer tubular cannula;

an inner tubular obturator having a distal portion sized for removable insertion within the outer tubular cannula so that the inner tubular obturator is positionable in a selected one of an open orientation and a closed orientation relative to the tissue collection region, where the obturator has a distal end, a proximal end separated from the distal end along an axis, a substantially cylindrical wall portion between the distal end and the proximal end, and a tissue collection orifice extending through the wall portion of said obturator; and a marker stylet having an outer surface, an inner surface, a distal end, and a proximal end separated from the distal end along an axis, the stylet being sized for removable insertion within the outer tubular cannula when the inner tubular obturator is not positioned within said outer tubular cannula, and wherein the stylet has a contrast agent chamber containing an air-filled void.

10. The biopsy needle of claim 9, wherein the marker stylet is made of a carbon-fiber composite material.

11. The biopsy needle of claim 10, wherein the carbon-fiber composite material is a substantially rigid material.

12. The biopsy needle of claim 9, wherein the marker stylet is made of a glass-fiber composite material.

13. The biopsy needle of claim 9, wherein the marker stylet is made of zirconia.

14. A biopsy needle, comprising:

an outer tubular cannula constructed of a substantially rigid material, said cannula having a distal end, a proximal end, a substantially cylindrical wall portion between the distal end and the proximal end, and an axis;

a tissue collection region at the distal end of the outer tubular cannula;

a marker stylet made of a substantially rigid material, the stylet being sized for removable insertion within the outer tubular cannula, and the stylet having an outer surface, an inner surface, a distal end, a proximal end separated from the distal end along an axis, and a contrast agent chamber containing a contrast agent, wherein the contrast chamber occupies a portion of a volume bounded by the outer surface, the distal end, and the proximal end.

15. The biopsy needle of claim 14, wherein the substantially rigid material is a carbon-fiber composite material.

16. The biopsy needle of claim 14, wherein the contrast agent is chosen from a group consisting of paramagnetic agents, superparamagnetic agents, ferrimagnetic agents, and ferromagnetic agents.

17. The biopsy needle of claim 14, wherein the contrast agent comprises a paramagnetic metal ion.

18. The biopsy needle of claim 14, wherein the contrast agent comprises an organic chelate of a paramagnetic metal ion.

19. The biopsy needle of claim 14, wherein the contrast agent comprises a chelate of gadolinium (III).

20. The biopsy needle of claim 14, wherein the contrast agent comprises Gd-DTPA.

21. A method for determining an optimal contrast agent volume and concentration for an invasive medical instrument for use with a diagnostic medical imaging system, wherein the system includes an imaging region and a means for producing an image of a target object in the imaging region, and wherein the instrument has a contrast media chamber occupying at least part of the body, the method including the steps of:

(a) positioning a test instrument in the imaging region, said test instrument having a carbon-fiber body substantially identical to the carbon-fiber body of the invasive medical instrument, and a test volume of contrast media at a test concentration, the contrast media contained in a contrast media chamber occupying at least part of the test body;

(b) operating the system to produce a test magnetic resonance image showing the test instrument;

(c) positioning at least one additional test instrument in the imaging region, wherein each said additional test instrument has a carbon-fiber test body substantially identical to the carbon-fiber body of the invasive medical instrument, said additional test instrument containing a different test volume or test concentration of contrast media, the contrast media contained in a contrast media chamber occupying at least part of the test body, wherein each said different volume or concentration differs from the first test volume or concentration, and wherein said first test volume or concentration and each said different volume or concentration together comprise a set of test volumes or concentrations, and said test instrument and said at least one additional test instrument together comprise a set of test instruments;

(d) operating the system to produce at least one additional test image showing each said additional test instrument, wherein said at least one additional test image and said test image together comprise a set of test images; and (e) identifying as the optimal contrast agent volume or concentration, the test volume or concentration which results in a test image having a desired positively shown representation of one of the test instruments.

22. The method of claim 21, wherein the target object is positioned in the imaging region with the test instrument during each of steps (a), (b), (c), and (d), wherein each said test image includes a representation of the target object, and wherein said desired positively shown representation of one of the test instruments does not significantly degrade the representation of the target object.

* * * * *